United States Patent [19]

Catalano

[11] Patent Number: 4,776,841
[45] Date of Patent: Oct. 11, 1988

[54] BILUMEN PERIPHERAL VENOUS CATHETER WITH ADAPTER

[76] Inventor: Marc L. Catalano, 2501 Bahama Dr., Miramar, Fla. 33023

[21] Appl. No.: 906,138

[22] Filed: Sep. 11, 1986

[51] Int. Cl.$^4$ ............................................. A61M 25/00
[52] U.S. Cl. ....................................... 604/43; 604/280
[58] Field of Search ................... 604/43, 44, 280, 283, 604/264

[56] References Cited

U.S. PATENT DOCUMENTS

| | | | |
|---|---|---|---|
| 4,568,329 | 2/1986 | Mahurkar | 604/43 |
| 4,583,968 | 4/1986 | Mahurkar | 604/43 |
| 4,626,240 | 12/1986 | Edelman et al. | 604/43 |
| 4,643,711 | 2/1987 | Bates | 604/43 |
| 4,675,004 | 6/1987 | Hadford et al. | 604/44 |
| 4,682,978 | 7/1987 | Martin | 604/43 |

Primary Examiner—Stephen C. Pellegrino
Attorney, Agent, or Firm—Robert M. Schwartz; Edward I. Mates

[57] ABSTRACT

Bilumen catheters of the present invention have two lumens to supply two non-miscible liquids simultaneously and a method for their use. The two lumens are enclosed within a single catheter and have different cross-sections, the lumen of larger cross-section not exceeding 18 gauge to infuse or remove higher viscosity fluids, such as blood, and the lumen of smaller cross-section designed to infuse or remove lower viscosity fluids. Catheters of this invention are more narrow than prior art catheters so that they need not be employed in the vicinity of the heart or other vital organs and may be used in peripheral portions of a patient's body, such as the patient's limbs. This invention reduces the likelihood of blood clots, dysarythmias and infection. They do not need highly trained individuals, such as doctors, for injection purposes, but may be used by any paramedic or nurse in an emergency. This invention also comprises an adapter of special construction that facilitates connecting said lumens simultaneously to sources of different fluids for simultaneous infusion thereof into a peripheral cavity of a patient.

9 Claims, 3 Drawing Sheets

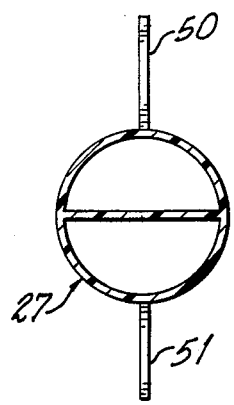
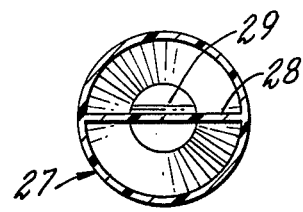
FIG-4.   FIG-5.
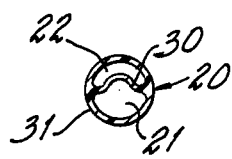
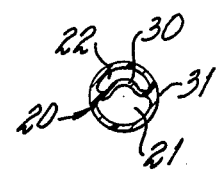
FIG-6.   FIG-7.
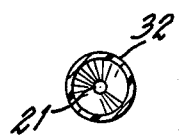
FIG-8.   FIG-9.
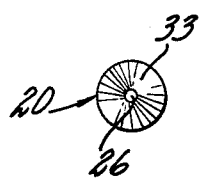
FIG-10.

BILUMEN PERIPHERAL VENOUS CATHETER WITH ADAPTER

BACKGROUND OF THE INVENTION

I. Field of the Invention

This invention relates to surgical instruments for introducing fluids into a cavity of a body. It has special utility in the simultaneous introduction of non-compatible fluids, particularly those that are non-miscible and those having different viscosities.

II. Description of the Related Art

A catheter is a tubular medical device that is inserted into vessels or body cavities to permit the injection or removal of fluids or substances or to maintain open a passageway within a body of a patient. The term "patient" is used to include animals as well as humans. In the past, catheters have been provided with one or more lumens, which are elongated tubes that are incorporated within the body of a catheter and extend in the form of a tube or a hollow needle.

One type of catheter used in the prior art is known as a central venous catheter. This type of catheter is generally inserted into the subclavien vein or the external jugular vein, all located within close proximity of a vital organ, such as the chest and heart. Usually the central venous catheter is a long cylindrical tube approximately 20 to 30 centimeters (8 to 12 inches) long and has a diameter of approximately 0.3 centimeters (⅛ inch). One type of central venous catheter is known as a tri-lumen central venous pressure line. Such a pressure line contains 3 lumens, each of which extends from an extended diaphragm to a trifurcation member where the 3 lumens are held together. Fluid of a unique characteristic desired to be imparted or injected into an individual patient is applied using a syringe to inject a different unique fluid into each of the 3 diaphragms. The 3 different fluids enter a respective lumen for further movement of the respective fluids towards their points of discharge into the body of the patient. Each lumen has a discharge point at different distances from the trifurcation point. The lumen that discharges fluid into the patient's body at the closest point to the trifurcation point is called "the proximal discharge point", the lumen having a middle discharge opening is termed "the medial discharge point" and the lumen whose discharge point is at the greatest distance from the trifurcation point is termed "the distal discharge point".

In prior art devices, the individual lumens had to be of sufficiently large cross-section to provide injection of 3 different fluids at 3 different spaced positions within the body of the patient. It was believed necessary to provide such injections in the vicinity of the large blood vessels near the heart and other vital organs of the patient. Such proximity to the vital organs rendered the insertion of catheters a dangerous job, which made it necessary that a highly trained and highly skilled person, such as a doctor, had to perform the insertion of the catheter.

Double current catheters suitable for removing blood from a fistula or vein for processing in a dialysis machine and returning the processed blood back to the fistula or vein is disclosed in U.S. Pat. Nos. 4,134,402 to Mahurkar. Another double lumen catheter provided with additional features to promote insertion and to perform a dilator function is disclosed in U.S. Pat. No. 4,568,329 to Mahurkar. The patents to Mahurkar disclose double lumen continuous flow hemodialysis needles and cannulae having contiguous lumens of different lengths formed by dividing a unitary straight tube with an internal longitudinal septum. The shorter lumen acts as a blood intake lumen and the longer lumen acts as a blood return lumen. In the Mahurkar patents, the catheters are divided into semicircular lumens of equal cross-section extending side by side for a major portion of the length of the catheter. In only a short portion at the distal end of the catheter do the lumens have different cross-sections.

Numerous other U.S. patents disclose double current catheters for hemodialysis that evidence a long felt need for a small, functionally efficient catheter, having a minimum of insertion trauma and potential for clotting. U.S. Pat. No. 4,096,860 to McLaughlin discloses a coaxial hemodialysis catheter said to allow a step enlargement of the opening of a blood vessel to avoid its tearing and rupture along its side walls. A simultaneous flow device incorporates a hub with an extension conduit and a valve to receive a needle therethrough. The extension conduit is sufficiently large to allow the needle to pass therethrough adjacent the interior side walls with an attendant extension thereof from its opening. The needle with the extension conduit is adapted for combined insertion within a blood vessel, after which it can be withdrawn while the valve prevents the backflow of blood through the axial passage of the hub. A coaxial flow device can then be inserted within the hub conduit.

U.S. Pat. No. 4,099,528 to Sorenson et al discloses a coaxial double lumen cannula mounted upon a hub and having a central stylet needle to penetrate a patient's vein and which is retractable after penetration.

U.S. Pat. No. 4,203,436 to Grimsrud discloses a hollow hypodermic needle with a divider to provide a first channel to remove blood for treatment from a punctured blood vessel and a second channel to return the treated blood to the blood vessel.

U.S. Pat. No. 4,385,631 to Uthmann discloses a hemodialysis catheter to puncture blood vessels. The Uthmann device includes a section insertable through a puncture opening into a blood vessel and a hose line following thereafter.

U.S. Pat. No. 4,403,983 to Edelman et al discloses a dual lumen cannula in the form of a tube divided longitudinally throughout essentially its entire length by a septum to create two parallel lumens of equal cross-section, one for withdrawing blood from the subclavian vein for extra corporeal processing and the other to return the treated blood back to the subclavian vein in the area of blood withdrawal.

U.S. Pat. No. 4,180,068 to Jacobson et al discloses a double current hemodialysis catheter comprising a primary tube and an internal divider which also functions as a trocar and valve. The primary tube has a side opening to receive blood and a central opening at the distal end of the primary tube. The internal divider includes a cutting end which protrudes from the distal opening when the divider is longitudinally moved to an insert position. In the insert position, blood flow is blocked.

U.S. Pat. No. Des. 272,651 to Mahurkar discloses a double lumen catheter having an outlet lumen which has an opening at the tip of the catheter and a shorter inlet lumen which terminates in a bevel substantially displaced from the tip of the catheter.

None of the patents described provide a catheter having a cross-section sufficiently small to encompass a plurality of small cross-section lumens which are capable of insertion into a peripheral portion of a patient's body such as the arm or leg of a patient so that different fluids which are non-miscible with one another can be applied in spaced relation within the patient's body using peripheral venous catheters, while maintaining integrity and independence of each of a plurality of injected fluids or medications being simultaneously applied to the patient.

SUMMARY OF THE INVENTION

The present invention makes it unnecessary to insert a catheter in the vicinity of a dangerous part of a patient's body; namely the vicinity of the heart and other critical organs. The present invention provides catheters that enclose a primary lumen of such small cross-section that it may be inserted into a patient's body in a peripheral, non-critical portion thereof, such as an arm or a leg, simultaneously with application of another material of lesser viscosity which is applied through a secondary lumen.

The present invention divides a catheter into lumens of different cross-sections. The primary lumen has a relatively large cross-section throughout its length sufficient to permit the application or injection of high viscosity fluids, whereas the secondary lumen enclosed within the catheter has a smaller cross-section and a more proximal opening through which low viscosity fluids can be applied. The ratio of cross-sections of said primary and secondary lumens remains essentially constant from the hub of the catheter to the proximal opening at the distal end of the secondary lumen.

Prior art dual lumen catheters that infuse and remove blood require a cross-section of catheter that is at least double the 18 gauge lumens required for the input and removal of blood. The present invention, which flows blood and a less viscous fluid in adjacent lumens simultaneously, requires only the blood supplying lumen have an 18 gauge, the other lumen for supplying the less viscous fluid can be as small as 26 gauge and still pass non-viscous fluids. Therefore, the cross-section of the present invention type of catheter need be only slightly more than one half of the required cross-section of prior art dual flow catheters. This feature enables the catheter of the present invention to be inserted into smaller blood vessels than is possible with prior art dual flow catheters, and causes considerably less discomfort to insert than prior art catheters.

Another benefit of the present invention is that is enables people who do not have the training and experience of physicians or surgeons to insert the catheter of the present invention without danger to the patient, because the smaller diameter bilumen catheters of the present invention may be inserted into peripheral portions of the body such as a patient's arm or leg rather than in the vicinity of a vital organ. Therefore, the catheters of the present invention do not represent as much danger to the patient as prior art bilumen catheters, whose larger cross-sections limit their infusion into large diameter blood vessels located near vital organs, such as the heart.

Still another feature of the present invention is the inclusion of flexible extension wings which wrap around the wrist or ankle or limb of the patient and allows the catheter to be taped in place in a location spaced from the catheter needle. In a preferred embodiment, the wings extend transversely from a hub at the proximal end of the catheter in opposite directions for securement to the wrist, ankle or limb from that occupied by the hub. This feature reduces the possibility of contaminating the needle of the catheter and causing infection that would be harmful to the patient.

The present invention is also provided with flexible securing clips especially constructed and arranged to enable the catheter to be secured to an adapter quickly and to enable the adapter to be released from the catheter quickly, easily and cleanly. In a preferred embodiment of this invention, the flexible securing clips extend in a proximal direction from the hub to be secured to an adapter, whose purpose will be described.

The present invention also comprises an adapter of novel construction which cooperates with the hub constructed and arranged in a special manner to facilitate the simultaneous connection of individual, discrete supply tubes to corresponding lumens of a multilumen catheter or to a single lumen catheter and which also makes possible the ready disconnection of said catheter from said supply tubes.

Finally, the opening at the distal end of the secondary lumen that extends only part of the length of the catheter is both bevelled and slanted relative to the elongated axis of the catheter. this feature allows the catheter to be inserted easily into a vein of an arm or leg of a patient. In the prior art, proximal and medial openings of catheters provided with a multiplicity of lumens were only bevelled, and not slanted.

The aforesaid benefits of the present invention will be better understood in the light of a description of preferred embodiments that follow.

BRIEF DESCRIPTION OF THE DRAWINGS

In the drawings that form part of the description of the present invention,

FIG. 4 is a cross-sectional view along the line 4—4 of FIG. 1;

FIG. 5 is a cross-sectional view along line 5—5 of FIG. 1;

FIG. 6 is a cross-sectional view along line 6—6 of FIG. 1 or FIG. 3;

FIG. 7 is a cross-sectional view along line 7—7 of FIG. 1 or FIG. 3;

FIG. 8 is a cross-sectional view along line 8—8 of FIG. 1 or FIG. 3;

FIG. 9 is a cross-sectional view along line 9—9 of FIG. 1 or FIG. 3;

FIG. 10 is an end view along line 10—10 of FIG. 1 or FIG. 3;

Referring now to FIGS. 1, 2 and 4 to 10, a preferred embodiment of the present invention is disclosed. These drawings show a dual inflow double lumen catheter 20 conforming to the present invention and an adapter 40 of special construction. The catheter is of elongated construction containing a cylindrical shaped proximal portion 31, a medial portion 32, which, in turn, merges into a distal portion 33 of narrow frustoconical shape. Catheter 20 contains a primary lumen 21 preferably of 18 gauge side by side with a secondary lumen 22 preferably of 26 gauge. Medial portion 32 comprises a proximal opening 23 that has an inward bevel 24 merging into an outwardly slanted portion 25. Opening 23 extends through the wall of the catheter 20 to provide a discharge point for the secondary lumen 22. The primary lumen 21 extends to the distal opening 26 at the distal end of the catheter 20. The outer wall of the catheter 20 is of cylindrical shape throughout the cylindrical proximal portion 31 and then is apertures in the medial portion 32, which merges into the distal portion 33.

Figure 1:
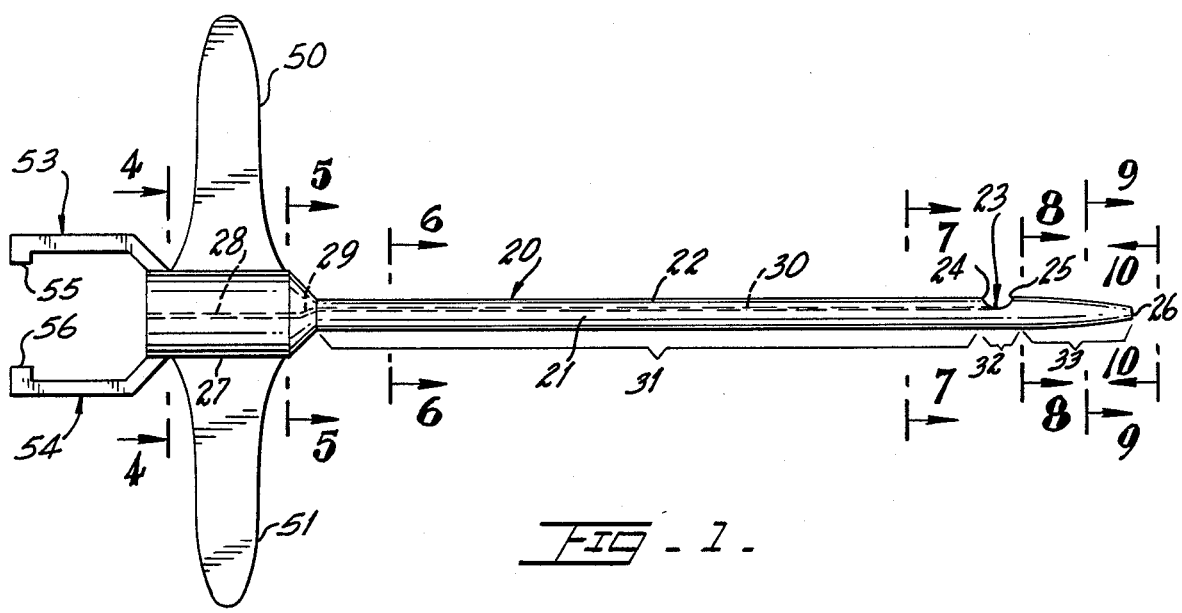
FIG. 1 is a longitudinal view of a bilumen peripheral venous catheter conforming to one embodiment of the present invention.

A hub 27 having an open end forming a proximal opening of circular cross-section (See FIG. 4) beyond the proximal end of the cylindrical proximal portion 31 of the catheter 20 extends axially from the proximal end of catheter 20. The interior of the hub 27 is provided with a thick divider wall portion 28 extending axially longitudinally and diametrically transversely merging into a veering wall portion 29 at the distal end of hub 27 to divide the hub into chambers. Veering wall portion 29 extends into a divider wall 30 that divides substantially the entire length of the catheter into the lumens 21 and 22 of different cross-section, preferably conforming to 18 gauge and 26 gauge, respectively, as shown in section in FIGS. 5, 6 and 7. Within hub 27, divider wall portion 28 forms a septum that separates hub 27 into chamber portions that are semi-circular and of equal diameter at the portions of hub 27 that intersect the planes of FIGS. 4 and 5. Veering wall portion 29 veers obliquely and changes shape gradually from a straight wall portion 28, shown in cross-section in FIG. 5 to the arcuately shaped divider wall portion 30 of FIGS. 6 and 7.

Figure 2:
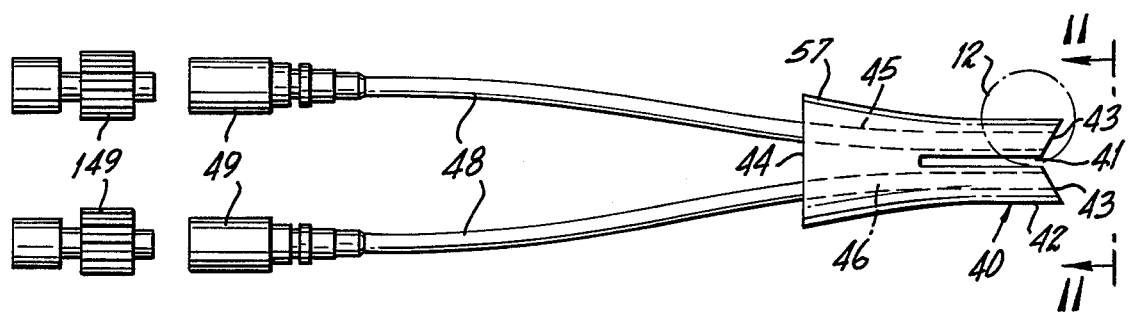
FIG. 2 is a longitudinal view of one type of adapter provided with a bifurcated distal end that engages the proximal end of a hub at the proximal end of the catheter of FIG. 1.
Figure 11:
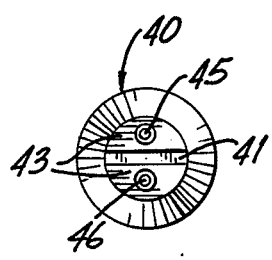
FIG. 11 is a sectional view along line 11—11 of FIG. 2.
Figure 12:
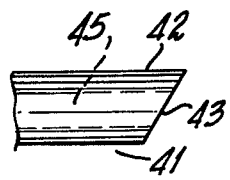
FIG. 12 is an enlargement of circular area 12 at the distal end portion of one portion of one of the bifurcated members of the adapter of FIG. 2.

FIGS. 2, 11 and 12 show a bifurcated adapter 40 which is provided with a central recess 41 that receives the divider wall portion 28 when the bifurcated adapter 40 is inserted into the hub 27. An annular ring 42 encircles recess 41 at the distal end of the adapter 40. Each bifurcation of adapter 40 has an oblique distal wall 43. Adapter 40 has a flat proximal end wall 44. Discrete passages 45 and 46 through adapter 40 of different cross-sections, extend through adapter 40. Each discrete passage 45 or 46 flanks the central recess 41. The distal end walls 43 of the bifurcations that flank recess 41 are oblique. Passages 45 and 46 extend from their proximal ends to a pair of tubes 48 that terminate in detachable diaphragms 49. The latter are constructed for coupling and decoupling with a pair of adapters 149 (see FIG. 2). Adapters 149 are provided at the distal ends of fluid supply means (FIG. 2) constructed and arranged to connect tubes 48 via detachable diaphragms 49 and adapters 149 to first and second fluid storage means (not shown) for storing fluids of different viscosities, such as relatively high viscosity blood and a relatively low viscosity nutrient. Thus, the fluids are delivered to lumens 21 and 22 for parallel discrete flows therethrough in the same direction. A viscous liquid such as blood is injected by a needle through one of the diaphragms 49 for flow along tube 48 through the passage 46 of bifurcated adapter 40 and through one of the chambers of hub 27 through primary lumen 21 for discharge through distal end opening 26 into the cavity of a patient. Simultaneously, a low viscosity fluid can be injected from secondary lumen 22, which is of smaller cross-sectional area than the primary lumen 21 through the other diaphragm 49, the other tube 48, passage 45 and the other chamber of hub 27. Having the distal end walls 43 of adapter 40 oblique facilitates alignment of passages 45 and 46 with lumens 21 and 22 when central recess 41 engages wall portion 28.

The hub has attached thereto a pair of transversely extending flexible elongated extension wings 50 and 51 which are adapted to flex to conform to a peripheral limb of the patient and to extend around said limb. This feature allows catheter 20 to be fixed in position relative to the patient's limb by taping the extension wings 50 and 51 to said limb in spaced relation to the location where the needle of the catheter enters through the skin of the patient. The separation of the area of attachment from the point where the needle of the catheter penetrates into the patient's body minimizes contamination of the infusion site.

In addition, flexible securing clips 53 and 54 (FIG. 1) extend proximally from the proximal end of the bifurcated hub 27 and are provided with inturned ends 55 and 56. The securing clips 53 and 54 and their attached inturned ends 55 and 56 ae flexible. The adapter 40 has an oblique outer wall 57 which diverges in the proximal direction. This divergence forces the flexible securing clips 53 and 54 apart as the bifurcated adapter 40 is inserted into the space flanking the divider wall portion 28 of hub 27. The inturned ends 55 and 56 snap over the proximal flat wall 44 of the annular ring 42 when adapter 40 is fully inserted in hub 27. When it is desired to disconnect the adapter 40 from the hub 27, an outer pull of the adapter 40 causes the end portions 55 and 56 to separate readily from one another as the flexible securing clips 53 and 54 permit easy removal of the adapter 40.

It is noted that the outer wall of catheter 20 in the vicinity of the proximal opening 23 at the end of the secondary lumen 22 is both inwardly bevelled at 24 and outwardly slanted at 25 in the distal direction toward the portion of the catheter that forms narrow conically-shaped end portion 33, merging from a cylindrically shaped proximal portion 31 along the major portion of the length of the catheter 20. The fact that the lumen opening 23 is both bevelled and slanted relative to the length of the catheter allows easier insertion and removal of the catheter into a blood vessel of a patient when the catheter is of the bilumen type that simultaneously infuses or removes two different, non-compatible fluids to or from a single body cavity.

Figure 3:
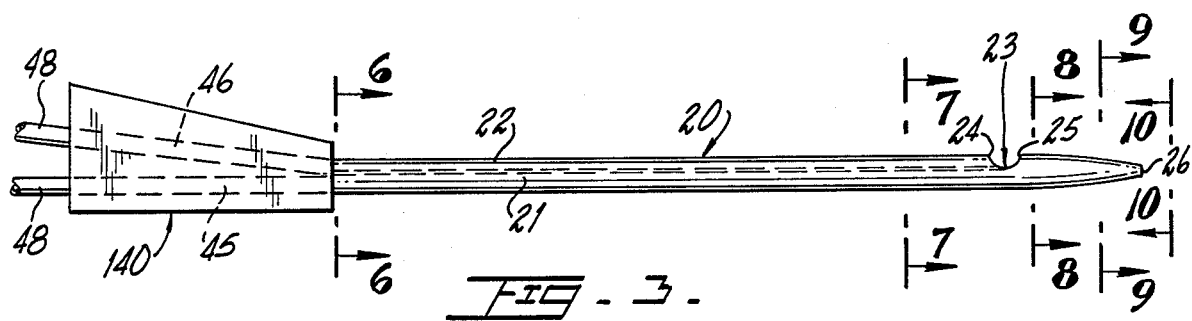
FIG. 3 is a view similar to that of FIG. 1 and FIG. 2, showing an alternate construction of catheter and hub.

FIG. 3 shows a modified embodiment of this invention in which a modified adapter 140 has passages 45 and 46 extending its full length with passage 45 widening to conform to the wider cross-section of primary lumen 21 and passage 46 narrowing to conform to the narrower cross-section of secondary lumen 22 at the distal end of modified adapter 140. Thus, non-miscible fluids supplied separately through tubes 48 and passages 45 and 46 to primary lumen 21 and secondary lumen 22 are imparted simultaneously and independently in parallel paths in the same direction and are kept from mixing until both liquids enter the body of a patient undergoing treatment.

Figure 13:
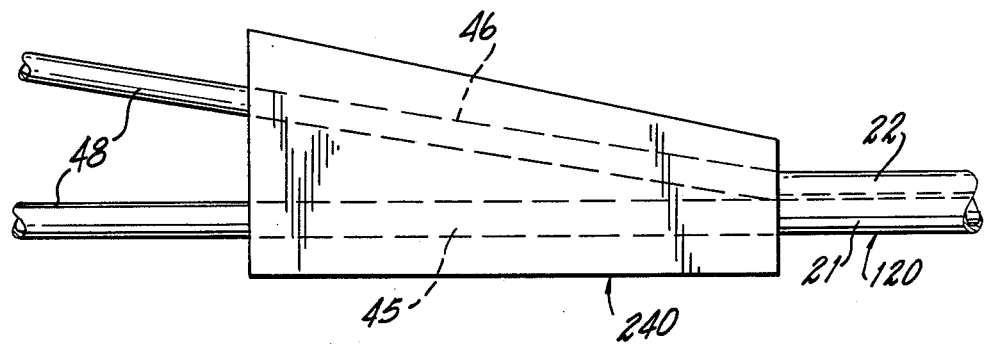
FIG. 13 is an enlarged view of the left-hand portion of FIG. 3.

It is understood that while the present invention shows a bifurcated adapter 40 connecting two separated passages 45 and 46 to two separate lumens 21 and 22, the number of separate passages and corresponding number of lumens may be increased or decreased without departing from the gist of the present invention. Also, if two or more miscible liquids are supplied through separate passages, the passages may merge within the distal end portion of the adapter to feed a mixture of said miscible liquids before said mixture reaches or at the time said miscible liquids mixture reaches the proximal end of said catheter without departing from the gist of this invention as it pertains to either embodiment of adapter shown in FIG. 2 or FIG. 3. In FIG. 13, the distal end of an adapter 240 forms a friction fit with a catheter 120.

The present invention is used to simultaneously apply a relatively thin, free flowing liquid, such as a medicinal solution, through a lumen having a relatively small cross-section and terminating at a proximal opening that is both bevelled and slanted in cooperation with a primary lumen of larger cross-section not exceeding 18 gauge for infusing a higher viscosity liquid, such as blood, that extends the full length of the catheter and permits the insertion of a catheter end portion having a reltively narrow cross-section which is all that is needed for insertion into peripheral portions of the body, such as the limbs. The bilumen peripheral venous catheters of this invention are also useful in simultaneously infusing different fluids that are non-miscible even though their viscosities are equal or almost equal.

According to the provisions of the patent statutes, the preferred construction and mode of operation of the present invention has been explained and what is now considered to be its best embodiments have been illustrated and described. However, it should be understood that, within the scope of the claimed subject matter that follows, the invention may be practiced otherwise than as specifically illustrated and described.

What is claimed is:

1. A bilumen peripheral venous catheter comprising
  an elongated tube with an outer wall, a proximal cylindrical portion having an internal divider wall to separate said proximal cylindrical portion into a primary lumen of relatively large cross-section not exceeding 18 gauge and a secondary lumen of relatively small cross-section,
  said lumens extending in side by side relation along the length of said proximal cylindrical portion,
  a distal tube portion of narrow truncated conical configuration enclosing the distal end portion of said primary lumen extending beyond the distal end of said proximal cylindrical portion,
  a medial tube portion extending in a cylindrical configuration from its proximal end conforming to that of the distal end of said proximal cylindrical portion to said distal tube portion,
  an opening in the outer wall of said medial tube portion of said elongated tube communicating with the distal end of said secondary lumen for infusing said first fluid from said secondary lumen; and
  an opening at the distal end of said distal tube portion for simultaneously infusing said second fluid from said primary lumen.

2. In combination with the catheter as set forth in claim 1, first fluid storage means for storing a relatively high viscosity fluid, second fluid storage means for storing a relatively low viscosity fluid,
  means constructed and arranged to connect said primary lumen to said first fluid storage means and means constructed and arranged to connect said secondary lumen to said second fluid storage means, whereby to supply said first fluid to said primary lumen from said first fluid storage means and to supply said second fluid to said secondary lumen from said second fluid storage means for delivery through said lumens in discrete parallel paths in the same direction.

3. A bilumen peripheral venous catheter comprising
  an elongated tube with an outer wall, a proximal cylindrical portion having an internal divider wall to separate said proximal cylindrical portion into a primary lumen of relatively large cross-section and a secondary lumen of relatively small cross-section,
  said lumens extending in side by side relation along the length of said proximal cylindrical portion,
  a distal tube portion of narrow truncated conical configuration enclosing the distal end portion of said primary lumen extending beyond the distal end of said proximal cylindrical portion,
  a medial tube portion extending in a cylindrical configuration from its proximal end conforming to that of the distal end of said proximal cylindrical portion to said distal tube portion,
  an opening in the outer wall of said medial tube portion of said secondary lumen for infusing a first fluid from said secondary lumen, and
  an opening at the distal end of said distal tube portion for simultaneously infusing a second fluid from said primary lumen, and further including a hub having a divider wall portion adjacent the proximal end of said catheter,
  an adapter having a recess flanked by adapter walls having passages,
  a supply tube connected to each of said passages,
  said adapter being constructed and arranged to enable said recess to receive said divider wall portion when said adapter is inserted into said hub,
  said divider wall portion merging into a veering wall portion that, in turn, merges into said internal divider wall, whereby liquid supplied to one of said supply tubes flows simultaneously through its corresponding passage to one of said lumens and a different liquid supplied to the other of said supply tubes flows through said other corresponding passage to the other of said lumens.

4. A catheter as set forth in claim 3, wherein one of said lumens terminates in a proximal outer wall opening of said catheter in a medial portion of said catheter that is both bevelled and slanted with respect to the longitudinal axis of said catheter to facilitate its insertion in and removal from the body of a patient.

5. A catheter as set forth in claim 4, wherein the other of said lumens terminates at said opening at the distal end of said catheter.

6. A catheter as set forth in claim 3, further including a pair of flexible extension wings extending radially in opposite directions from said hub, said wings being constructed and arranged to extend around a limb of a patient a sufficient distance to be secured to said limb in spaced relation to the point where said catheter penetrates into the body of said patient.

7. A catheter as set forth in claim 3, wherein said adapter has an oblique outer wall and a flat proximal end wall and a pair of flexible securing clips extend from the proximal end of said hub to engage against said oblique outer wall in sliding engagement thereagainst and separate from one another when said recess of said adapter receives the proximal end portion of said divider wall portion.

8. A catheter as set forth in claim 7, wherein each of said flexible securing clips has an inturned end portion constructed and arranged to engage said flat proximal end wall of said adapter when said recess engages said divider wall portion.

9. A catheter as set forth in claim 3, wherein said lumen of relatively large cross-section has a cross-section not exceeding 18 gauge.

* * * * *

UNITED STATES PATENT AND TRADEMARK OFFICE
CERTIFICATE OF CORRECTION

PATENT NO. : 4,776,841
DATED : October 11, 1988
INVENTOR(S) : Marc L. Catalano

It is certified that error appears in the above—identified patent and that said Letters Patent is hereby corrected as shown below:

Claim 1 lines 20-21 (corresponding to column 7 lines 57-58 of the issued patent), change "said first" to -- a second --.

Claim 1 line 23 (corresponding to column 7 line 60), change "said second" to -- a first --.

Claim 3 line 18 (corresponding to column 8 line 25), change "first" to -- second --.

Claim 3 line 21 (corresponding to column 8 line 28), change "second" to -- first --.

Signed and Sealed this

Thirty-first Day of March, 1992

Attest:

HARRY F. MANBECK, JR.

*Attesting Officer*     *Commissioner of Patents and Trademarks*